United States Patent [19]

Merce-Vidal et al.

[11] Patent Number: 5,292,739
[45] Date of Patent: Mar. 8, 1994

[54] ARYL(OR HETEROARYL) PIPERAZINYLALKYLAZOLE DERIVATIVES, THEIR PREPARATION AND THEIR APPLICATION AS MEDICAMENTS

[75] Inventors: Ramon Merce-Vidal; Jordi Frigola-Constansa; Juan Pares-Corominas, all of Barcelona, Spain

[73] Assignee: Laboratorios del Dr. Esteve, S.A., Barcelone, Spain

[21] Appl. No.: 825,929

[22] Filed: Jan. 27, 1992

[30] Foreign Application Priority Data

Jan. 28, 1990 [FR] France ................. 90 00923

[51] Int. Cl.$^5$ ............... A61K 31/495; C02D 403/00
[52] U.S. Cl. .................... 514/253; 514/252; 514/254; 544/295; 544/366; 544/370; 544/371; 544/372
[58] Field of Search ........... 544/295, 366, 370, 372, 544/371, 362, 373; 514/252, 253, 254; A61K 31/495

[56] References Cited

U.S. PATENT DOCUMENTS

| | | | |
|---|---|---|---|
| 3,362,956 | 1/1968 | Archer | 260/268 |
| 3,472,854 | 10/1969 | Archer | 260/268 |
| 3,472,855 | 10/1969 | Archer | 260/268 |
| 3,511,841 | 5/1970 | Archer | 260/268 |
| 3,562,278 | 3/1971 | Archer | 260/268 |
| 4,547,499 | 10/1985 | Hester, Jr. | 514/235 |
| 5,128,343 | 7/1992 | Pinol et al. | 544/295 |

FOREIGN PATENT DOCUMENTS

| | | |
|---|---|---|
| 0379990 | 1/1990 | European Pat. Off. |
| 0382637 | 2/1990 | European Pat. Off. |
| 0407844 | 6/1990 | European Pat. Off. |
| 1551082 | 10/1967 | France . |
| 1117068 | 11/1966 | United Kingdom . |
| 2155925 | 5/1985 | United Kingdom . |

OTHER PUBLICATIONS

Costall et al, The Journal of Pharmacology and Experimental Therapeutics (1992) vol. 262, No. 1, pp. 90–98.
Chemical Abstracts 104(23):752 (1986), Abstract No. 199305x.

*Primary Examiner*—Cecilia Tsang
*Attorney, Agent, or Firm*—Dressler, Goldsmith, Shore & Milnamow, Ltd.

[57] ABSTRACT

The present invention relates to heterocyclic compounds, characterized in that they have the general formula I

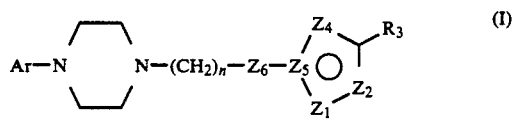

wherein Ar, n and $Z_1$–$Z_6$ are defined in the specification, are disclosed to have pharmaceutical activity on the central nervous system.

8 Claims, No Drawings

ARYL(OR HETEROARYL) PIPERAZINYLALKYLAZOLE DERIVATIVES, THEIR PREPARATION AND THEIR APPLICATION AS MEDICAMENTS

The present invention relates to new 1-{4-[4-(2-aryl (or heteroaryl))-1-piperazinyl]-alkyl}-1H-azole derivatives, a process for preparing them and their application as medicaments.

The compounds which are the subject of the present invention may be used in the pharmaceutical industry as intermediates and for the preparation of medicaments.

1-{4-[4-(aryl(or heteroaryl))-1-piperazinyl]-alkyl}-N-heterocyclyl diones are already known, for example:

Wu Y. H. et al., *J. Med. Chem.* 1969, 12, 876; Wu Y. H. et al., *J. Med. Chem.* 1972, 15, 477; Temple D. L. et al., U.S. Pat. No. 4,456,756; Yevich J. P. et al., *J. Med. Chem.* 1983, 26, 194; but, on the other hand, in the case of the azoles only our own publications are found (French Patent, A. Colombo et al., FR 2,642,759).

We have now discovered that the new 1-{4-[4-(2-aryl (or heteroaryl))-1-piperazinyl]-alkyl}-1H-azole derivatives, and their physiologically acceptable salts, which are the subject of the present invention have a pharmacological activity on the central nervous system; in particular they have anxiolytic and tranquillising activities, as well as an antidepressant activity, in the prevention of the abstinence syndrome and in disorders associated with cognition, such as senile dementia, memory dysfunction, impairment of consciousness, and the like, and, especially on the cardiovascular system, an antihypertensive activity. The new compounds which are the subject of the present invention may be used in medicine in the treatment of anxiety, depression, the abstinence syndrome, cognition disorders and hypertension.

The compounds which are the subject of the present invention have the general formula I

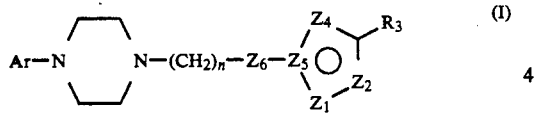
(I)

in which
Ar represents an aromatic radical, which may or may not contain nitrogen and is chosen from differently substituted aryls, 2-pyrimidine, 2-N-methylimidazole and 3-(1,2-benzisotriazole), n may have the values 1 to 6,
$Z_1$ represents a nitrogen atom or a C-$R_1$ group,
$Z_2$ represents a nitrogen atom or a C-$R_2$ group,
$Z_4$ represents a nitrogen atom or a C-$R_4$ group,
$Z_5$ represents a nitrogen atom or a carbon atom,
$Z_6$ represents an aza group or a methylene group which are unsubstituted or substituted,
when $Z_5$ represents a nitrogen atom, $Z_6$ is a methylene group, which is substituted or unsubstituted, and when $Z_5$ is a carbon atom, $Z_6$ is an aza group which is substituted or unsubstituted,
and $R_1$, $R_2$, $R_3$ and $R_4$, which may be identical or with the proviso that different and may also form part of another aromatic or non-aromatic ring, represent a hydrogen atom, a halogen, a lower alkyl radical, a hydroxyl radical, a carboxyl radical, a carboxamido radical, an aklyl carboxylate radical or an aryl or substituted aryl radical, and when Ar is 2-pyrimidine and $Z_6$ is a methylene group, substituted or unsubstituted, the whole $Z_1$ to $Z_6$ forms a heterocyclic aromatic radical, chosen among the group comprising trisubstituted imidazole, benzimidazole, which is substituted or unsubstituted and imidazopyridine, which is substituted or unsubstituted, and their pharmaceutically acceptable acid addition salts, except for the compounds in which Ar is a phenyl, which is substituted or unsubstituted, $Z_5$ and $Z_2$ both represent a nitrogen atom, $Z_1$ represents a C-$R_1$ group and $Z_4$ represents a C-$R_4$ group, and $R_3$-$R_4$ form part of another aromatic ring.

The new derivatives of general formula I may be prepared, according to the invention, by any one of the following methods.

METHOD A

By reaction of a compound of general formula II

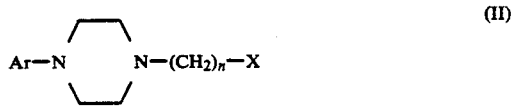
(II)

in which
Ar and n have the abovementioned meanings and X represents a halogen atom or a leaving group chosen from tosyloxy or mesyloxy, with a compound of general formula III

(III)

in which
$Z_1$, $Z_2$, $Z_4$ and $R_3$ have the abovementioned meanings.

The reaction takes place in the presence of a suitable solvent, for example dimethyl sulphoxide, dimethylformamide, an alcohol, an aromatic or non-aromatic hydrocarbon, an ether, such as dioxane or diphenyl ether, or a mixture of these solvents. This reaction is advantageously carried out in the presence of a base, such as alkali metal hydroxides, carbonates or bicarbonates, or a mixture of these bases.

The most suitable temperatures vary between ambient temperature and the reflux temperature of the solvent, and the reaction time is between 1 hour and 24 hours.

METHOD B

Method A is followed but, as the reaction leads to a mixture of isomers, the components are separated at the end of the reaction by means of physical methods, such as distillation, crystallisation or conventional chromatographic methods.

METHOD C

By reaction of a compound of general formula IV

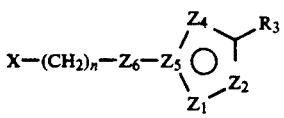 (IV)

in which
$Z_1$, $Z_2$, $Z_4$, $Z_5$, $Z_6$, $R_3$, n and X have the abovementioned meanings, with a compound of general formula V

 (V)

in which
Ar has the abovementioned meanings.

The reaction takes place in the presence of a suitable solvent, for example dimethyl sulphoxide, dimethylformamide, an alcohol, an aromatic or non-aromatic hydrocarbon, an ether, such as dioxane or diphenyl ether, or a mixture of these solvents. This reaction is advantageously carried out in the presence of a base, such as alkali metal hydroxides, carbonates or bicarbonates, or a mixture of these bases.

The most suitable temperatures vary between ambient temperature and the reflux temperature of the solvent, and the reaction time is between 1 hour and 24 hours.

METHOD D

By reaction of a compound of general formula VI

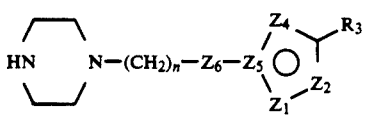 (VI)

in which
$Z_1$, $Z_2$, $Z_4$, $Z_5$, $Z_6$, $R_3$ and n have the abovementioned meanings, with a compound of general formula VII

in which
Ar and X have the abovementioned meanings.

The reaction takes place in the presence of a suitable solvent, for example dimethyl sulphoxide, dimethylformamide, an alcohol, an aromatic or non-aromatic hydrocarbon, an ether, such as dioxane or diphenyl ether, or a mixture of these solvents. This reaction is advantageously carried out in the presence of a base, such as alkali metal hydroxides, carbonates or bicarbonates, or a mixture of these bases.

The most suitable temperatures vary between ambient temperature and the reflux temperature of the solvent, and the reaction time is between 1 hour and 24 hours.

METHOD E

By reaction of a compound of general formula VIII

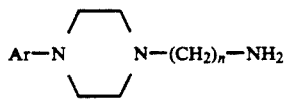 (VIII)

in which
Ar and n have the abovementioned meanings, with 2,5-dimethoxytetrahydrofuran.

The reaction takes place in the presence of a suitable solvent, for example dimethyl sulphoxide, dimethylformamide, dimethylacetamide or acetic acid.

The most suitable temperatures vary between 60° C. and 120° C. and the reaction time is between 5 minutes and 3 hours.

METHOD F

By hydrolysis of a compound of general formula I in which Ar, n, $Z_1$, $Z_2$, $Z_4$, $Z_5$, $Z_6$ and $R_3$ have the abovementioned meanings and where at least one of the substituents $R_1$, $R_2$. $R_3$ and $R_4$ represents an alkyl carboxylate group.

This reaction may take place either in a basic medium, preferably with the cooperation of an alkali metal base, such as sodium hydroxide or potassium hydroxide, at temperatures of between 40° C. and 100° C., or in an acid medium, preferably with hydrochloric acid, sulphuric acid or p-toluenesulfonic acid, at temperatures of between 40° C. and 100° C.

METHOD G

By reaction of a compound of general formula I in which Ar, n, $Z_1$, $Z_2$, $Z_4$, $Z_5$, $Z_6$ and $R_3$ have the abovementioned meanings, but where at least one of the substituents $R_1$, $R_2$, $R_3$ and $R_4$ represents a carboxyl radical, with an amino radical or an alkylamino radical, more particularly ammonia. This reaction may take place by methods already known from the literature, such as the mixed anhydride or the acid halide, amongst others.

The final condensation reaction with the amine takes place without a solvent or in the presence of a suitable solvent, for example in an aromatic hydrocarbon, such as benzene or toluene, a chlorinated compound, such as methylene chloride or chloroform, a ketone, an ether or an amide, such as dimethylformamide, or mixtures of these solvents. In addition, the presence of an inorganic base, such as sodium carbonate, or an organic base, such as pyridine or triethylamine, is desirable.

The appropriate temperatures vary between −10° C. and the boiling point of the solvent and the reaction time is between 1 hour and 24 hours.

METHOD H

By reduction of a compound of general formula IX, prepared by a method entirely similar to that of Method C,

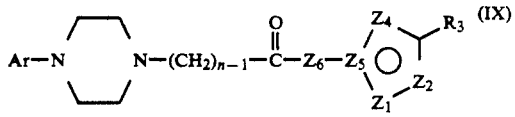 (IX)

in which

Ar, $Z_1$, $Z_2$, $Z_4$, $Z_5$, $Z_6$, $R_3$, and n have the abovementioned meanings.

The reaction preferably takes place with the cooperation of a metal hydride, such as lithium aluminium hydride, in a suitable solvent, for example an ether, such as diethyl ether or tetrahydrofuran. The temperature is kept between 25° and 40° C. during the addition and between ambient temperature and the reflux temperature of the solvent during the reaction. The reaction time is between 1 hour and 24 hours.

METHOD I

By reaction of a basic compound of general formula I with a non-toxic inorganic or organic acid in a suitable solvent, which may be, for example, an alcohol, such as methanol, ethanol or any of the propanols or butanols, an ester, such as ethyl acetate, or a nitrile, such as acetonitrile, and following the customary techniques of precipitation, crystallisation, etc., the corresponding salt is obtained.

The inorganic acid is chosen, inter alia, from hydrochloric acid, sulphuric acid, phosphoric acid and the acid metal salts, such as potassium hydrogen sulphate, and the organic acid is chosen from mono-, di- or tricarboxylic acids, for example acetic, lactic, malonic, succinic, glutaric, fumaric, malic, tartaric, citric, ascorbic, maleic, benzoic, phenylacetic, cinnamic and salicylic acids and sulphonic acids. It is possible to form the mono- or di-acid salt and these salts may or may not be in the form of a hydrate.

The preparation of new derivatives according to the invention is indicated in the following examples. A few use forms will also be described.

The following examples, which are given solely by way of illustration, in no respect imply any limitation of the scope of the invention.

METHOD A

EXAMPLE 16

Preparation of 1-{4-[4-(2-pyrimidinyl)-1-piperazinyl]-butyl}-1H-benzimidazole

A mixture of 6 g (20 mmol) of 2-[4-(4-bromobutyl)-1-piperazinyl]-pyrimidine, 2.36 g (20 mmol) of benzimidazole and 4.1 g (30 mmol) of potassium carbonate in 60 ml of dimethylformamide is refluxed for 14 hours. The reaction mixture is evaporated under vacuum, chloroform is added, the mixture is washed with water, dried over sodium sulphate and evaporated under vacuum and 4.8 g of 1-{4-[4-(2-pyrimidinyl)-1-piperazinyl]-butyl}-1H-benzimidazole are obtained, which may be recrystallised from ethyl ether, with a melting point of 85°- 88° C.

The compounds identified by Examples 2 to 16, 20, 23, 25 to 31, 36 to 41, 43 and 44 are obtained by the same procedure and the data for their identification are given in Tables I, II and III.

METHOD B

EXAMPLES 17 and 18

Preparation of 1-{4-[4-(2-pyrimidinyl)-1-piperazinyl]-butyl}-3H-imidazo [5,4-b]pyridine and 1-{4-[4-(2-pyrimidinyl) -1-piperazinyl]-butyl}-1H-imidazor[4,5-b]pyridine.

Method A is followed except that 1H-imidazo[4,5-b]pyridine is used as starting material.

A mixture of these two components is thus obtained, which is separated by high-pressure preparative chromatography.

The compounds identified by Examples 17 to 19, 21, 22 and 24 are obtained by a similar method and the data for their identification are given in Table 1.

METHOD C

EXAMPLE 35

Preparation of 4-chloro-1-[4-(4-phenyl-1-piperazinyl)-butyl]-1H-pyrazol

A mixture of 3.56 g (15 mmol) of N-(4-bromo-butyl)-4-chloropyrazole, 2.43 g (15 mmol) of 1-phenyl-piperazine and 2.76 g (20 mmol) of potassium carbonate in 50 ml of dimethylformamide is refluxed for 24 hours. The reaction mixture is evaporated under vacuum, chloroform is added, the mixture is washed with water, dried over sodium sulphate and evaporated under vacuum and 3.1 g of 4-chloro-1-[4-(4-phenyl-1-piperazinyl)-butyl]-1H-pyrazole are obtained, which may be recrystallised from ethyl ether with a melting point of 58°-61° C.

The spectroscopic data for the identification of this product are given in Table II.

METHOD D

EXAMPLE 1

Preparation of 1-{4-[4-(2-pyrimidinyl)-1-piperazinyl]-butyl}pyrrole

A mixture of 4.14 g (20 mmol) of 1-[4-(piperazinyl)-butyl)pyrrole, 2.29 g (20 mmol) of 2-chloropyrimidine and 4.1 g (30 mmol) of potassium carbonate in 60 ml of dimethylformamide is refluxed for 5 hours. The reaction mixture is evaporated under vacuum, chloroform is added and the mixture is washed with water, dried over sodium sulphate and evaporated under vacuum and 3.3 g of 1-{4-[4-(2-pyrimidinyl)-1-piperazinyl]-butyl}pyrrole are obtained in the form of a liquid.

The spectroscopic data for the identification of this product are given in Table I.

METHOD E

EXAMPLE 1

Preparation of 1-{4-[4-(2-pyrimidinyl)-1-piperazinyl]-butyl}pyrrole

A mixture of 4 g (17 mmol) of 2-[4(4-aminobutyl)-1-piperazinyl]pyrimidine and 3.3 g of 2,5-dimethoxytetrahydrofuran in 10 ml of acetic acid is refluxed for 1 hour. The reaction mixture is poured into cold water, neutralized with 10% sodium hydroxide solution and extracted with chloroform, the extract is dried and evaporated and 2.2 g of 1-{4-[4-(2-pyrimidinyl)-1-piperazinyl]-butyl}pyrrole are obtained.

The products of Examples 32 to 34 are obtained by the same procedure.

The spectroscopic data for the identification of these products are given in Tables I and II.

METHOD F

EXAMPLE 6

Preparation of 4-carboxy-1-{4-[4-(2-pyrimidinyl)-1-piperazinyl]-butyl}pyrazole

A mixture of 4.4 g (12.2 mmol) of ethyl 1-{4-[4-(2-pyrimidinyl)-1-piperazinyl]-butyl}-1H-pyrazole-4-carboxylate in 50 ml of 2N HCl is refluxed for 4 hours. The mixture is cooled in an ice bath, neutralized with ammonia and extracted with chloroform. 3.4 g of 4-carboxy-1-{4-[4-(2-pyrimidinyl)-1-piperazinyl]-butyl}-1H-pyrazole with a melting point of 104°-105° C. are thus obtained.

The spectroscopic data for the identification of this product are given in Table I.

METHOD G

EXAMPLE 5

Preparation of 4-carboxamido-1-{4-[4-(2-pyrimidinyl)-1-piperazinyl]-butyl}-1H-pyrazole 1.1 g (10.3 mmol) of ethyl chloroformate are added slowly to a solution, cooled to 0° C., of 3.4 g (10.3 mmol) of 4-carboxy-1-{4-[4-(2-pyrimidinyl)-1-piperazinyl]-butyl}-1H-pyrazole, Example 6, and 1.04 g (10.3 mmol) of triethylamine in 90 ml of dimethylformamide. After 30 minutes a stream of dry ammonia is passed in, stirring is continued for 1 hour at 0° C. and the mixture is left to stand at ambient temperature for 2 hours and filtered, the product is washed with dimethylformamide, dried and evaporated and 1.5 g of 4-carboxamido-1-{4-[4-(2-pyrimidinyl)-1-piperazinyl]-butyl}-1H-pyrazole are obtained, which may be recrystallised from acetone, with a melting point of 124° C.

The spectroscopic data for the identification of this product are given in Table I.

METHOD H

EXAMPLE 45

Preparation of 1,3-dimethyl-5-{3-[4-(2-methoxyphenyl)-1-piperazinyl]-propylamino}-1H-pyrazole 0.5 g (13 mmol) of lithium aluminium tetrahydride are suspended in 100 ml of tetrahydrofuran and a solution of 3.9 g (11 mmol) of 1,3-dimethyl-5-{3-[4-(2-methoxyphenyl) -1-piperazinyl]-propionamido}-1H-pyrazole in 50 ml of tetrahydrofuran is added dropwise in the course of 30 minutes. The mixture is kept at ambient temperature during the addition and is then refluxed for 3 hours. The excess lithium aluminium hydride is destroyed, the insoluble inorganic fraction is filtered off, the tetrahydrofuran is removed, the product is dissolved in chloroform, washed with water, dried over anhydrous sodium sulphate and evaporated to dryness and 3 g (81%) of 1,3-dimethyl-5-{3-[4-(2-methoxyphenyl)-1-piperazinyl]-propylamino}-1H-pyrazol are obtained.

The spectroscopic data for the identification of this product are given in Table III.

METHOD I

EXAMPLE 42

Preparation of 4,5-dichloro-2-methyl-1-{4-[4-(2-pyrimidinyl)-1-piperazinyl]-butyl}-1H-imidazole citrate 5 g of 4,5-dichloro-2-methyl-1-{4-[4-(2-pyrimidinyl)-1-piperazinyl]-butyl}-1H-imidazole (Example 11) are dissolved in 50 ml of ethyl alcohol and a solution of 3.15 g of citric acid monohydrate in 20 ml of ethanol is added. The reaction mixture is stirred for 1 hour and allowed to crystallise at ambient temperature. 7.1 g of crystals having a melting point of 137°-138° C. are obtained, which correspond to 4,5-dichloro-2-methyl -1-{4-[4-(2-pyrimidinyl)-1-piperazinyl]-butyl}-1H-imidazole citrate.

The spectroscopic data for the identification of this product are given in Table III.

TABLE I

[Structure: pyrimidine-N-(CH2)4-piperazine-N with Z1, Z2, Z4, R3 substituents on a ring]

| Example | Z$_1$ | Z$_2$ | Z$_4$ | R$_3$ | m.p. | IR cm$^{-1}$ | NMR solvent | $^1$H-NMR (100 MHz), δ, J=Hz |
|---|---|---|---|---|---|---|---|---|
| 1 | CH | CH | CH | H | oil | 2941, 1585, 1547, 1500, 1360, 1260, 983, 724 (film) | CDCl$_3$ | 1.55(m, 2H); 1.77(m, 2H); 2.25–2.55(c.a. 6H); 3.70–4.05 (c.a. 6H); 6.13(t, J=2.0Hz, 2H) 6.47(t, J=4.7Hz, 1H); 6.65 (t, J=2.0Hz, 2H); 8.29(d, J=4.7Hz, 2H) |
| 2 | C—CH=CH—CH=CH—C | | C—CH=CH—CH=CH— | H | oil | 2941, 1586, 1547, 1511, 1484, 1402, 1359, 1307, 1260, 983, 750, 723 (film) | CDCl$_3$ | 1.6(m, 2H); 1.86(m, 2H); 2.27–2.45(c.a. 6H); 3.78 (t, J=5.2Hz, 4H); 4.30(t, J=7.1Hz, 2H); 6.43 (t, J=4.7Hz, 1H); 7.12–7.46 (c.a. 6H); 8.07(d, J=6.5Hz, 2H)8.26(d, J=4.7Hz, 2H) |
| 3 | C—CH=CH—CH=CH—C | | CH | H | oil | 2940, 1585, 1547, 1510, 1446, 1359, 1259, 983, 741 (film) | CDCl$_3$ | 1.54(m, 2H); 1.88(m, 2H); 2.37(c.a. 6H); 3.79(t, J=5Hz, 4H); 4.13(t, J=6.8Hz, 2H); 6.45(c.a. 2H); 6.9–7.1(c.a. 5H); 8.27(d, J=4.7Hz, 2H) |
| 4 | C—CH=CH—CH=CH—C | | CPh | H | oil | 2942, 1586, 1547, 1502, 1447, 1359, 1261, 984, 789, 757, 702 (film) | CDCl$_3$ | 1.38(m, 2H); 1.68(m, 2H); 2.10–2.40(c.a. 6H); 3.76 (t, J=5Hz, 4H); 4.11(t, J=7Hz, 2H); 6.41 (t, J=4.7Hz, 1H); 7.10–7.50(c.a. 13H); 7.79(m, 1H); 8.25(d, J=4.7Hz, 2H) |
| 5 | N | CH | CH | —C(=O)NH$_2$ | 124° C. | 3337, 3156, 1663, 1601, 1586, 1446, 1360, 980 (KBr) | DMSO-d$_6$ | 1.38(m, 2H); 2.3–2.5(c.a. 6H); 3.69 (m, 4H); 4.14(t, J=7Hz, 2H); 6.6(t, J=4.7Hz, 1H); 7.0 (broad, 1H); 7.7(broad, 1H); 7.89(s, 1H); 8.24(s, 1H); 8.35(d, J=4.6Hz, 2H) |
| 6 | N | CH | CH | —C(=O)OH | 104–105° C. | 3100, 2943, 1587, 1546, 1487, 1440, 1360, 1260, 797(film) | DMSO-d$_6$ | 1.40(m, 2H); 1.81(m, 2H); 2.23–2.49(c.a. 6H); 3.0 (broad, 1H); 3.64(m, 4H); 4.13(t, J=7Hz, 2H); 6.6 (t, J=4.7Hz, 1H); 7.7(s, 1H); 8.1(s, 1H); 8.33(d, J=4.7Hz, 2H) |
| 7 | N | CMe | CCF$_3$ | H | 71–75° C. | 2937, 2856, 1586, 1544, 1496, 1393, 1228, 1177, 1125, 981(KBr) | CDCl$_3$ | 1.57(m, 2H); 1.89(m, 2H); 2.32(s, 3H); 2.30–2.55(c.a. 6H); 3.82(t, J=5Hz, 4H); 4.10(t, J=7Hz, 2H); 6.25(s, 1H); 6.47(t, J=4.7Hz, 1H); 8.29(d, J=4.7, 2H) |
| 8 | CH | N | CPh | Ph | oil | 2942, 1585, 1547, 1505, 1445, 1360, 1307, 1260, 983, 774, 1307, 1260, (film) | CDCl$_3$ | 1.55(m, 4H); 2.16–2.42(c.a. 6H); 3.71–3.89 (c.a. 6H); 6.47(t, J=4.7Hz, 1H) 7.12–7.60(c.a. 11H); 8.27 (d, J=4.7Hz, 2H) |
| 9 | CPh | N | CPh | Ph | oil | 2942, 1585, 1307, 1260, 1445, 1360, 1307, 1260, 698 (film) | CDCl$_3$ | 1.55(m, 4H); 1.95–2.33(c.a. 6H); 3.69–4.07(c.a. 6H) 6.47(t, J=4.7Hz, 1H); 7.13–7.67(c.a. 15H); 8.26 (d, J=4.7Hz, 2H) |
| 10 | CMe | N | CPh | Ph | oil | 2942, 1585, 1547, 1500, 1446, 1393, 1260, 983, 760, 698 (film) | CDCl$_3$ | 1.43(m, 4H); 2.18–2.47(c.a. 9H); 3.72–3.76(c.a. 6H) 6.47(t, J=4.7Hz, 1H); 7.09–7.39(c.a. 10H); 8.26 (d, J=4.7Hz, 2H) |
| 11 | CMe | N | CCl | Cl | oil | 2942, 1586, 1547, 1500, 1447, 1359, 1259, 1245, 983 (film) | CDCl$_3$ | 1.45–1.84(c.a. 4H); 2.26–2.57(c.a. 9H); 3.74–4.05(c.a. 6H) 6.48(t, J=4.7Hz, 2H); 8.30(d, J=4.7Hz, 2H) |
| 12 | CEt | N | CH | H | oil | 2938, 1585, 1495, 1446, 1360, 983, 638 (film) | CDCl$_3$ | 1.34(t, J=7.1, 3H); 1.66(m, 4H); 2.31–2.72(c.a. 8H); 3.77–3.92 (c.a. 6H); 6.47(t, J=4.7Hz, 1H) 6.87(d, J=10Hz, 2H); 8.26(d, J=4.7Hz, 2H) |

TABLE I-continued

Structure:

![structure with pyridyl-piperazinyl-(CH₂)₄-N linked to Z₁=Z₂-R₃=Z₄ ring]

| Example | Z₁ | Z₂ | R₃ | Z₄ | m.p. | IR cm⁻¹ | NMR solvent | ¹H-NMR (100 MHz), δ = Hz |
|---|---|---|---|---|---|---|---|---|
| 13 | CPh | N | CH | H | oil | 2941, 1585, 1547, 1500, 1446, 1360, 1547, 1500, 774, 700 (film) | CDCl₃ | 1.45(m, 2H); 1.73(m, 2H); 2.19–2.42(c.a. 6H); 3.77 (t, J=5.1Hz, 4H); 4.01(t, J=7.3Hz, 2H); 6.47 (t, J=4.7Hz, 1H); 6.94–7.61(c.a. 7H); 8.27(d, J=4.7Hz, 2H) |
| 14 | CH | N | CH | O=C–COMe | 92–94° C. | 2800, 1713, 1585, 1544, 1483, 1360, 1223, 1117, 985 (KBr) | CDCl₃ | 1.45(m, 2H); 1.72(m, 2H); 2.29–2.39(c.a. 6H); 3.67–3.74 (c.a. 7H); 4.01(t, J=6.8Hz, 2H) 6.47(t, J=4.7Hz, 1H); 7.67 (s, 1H); 7.81(s, 1H); 8.24(d, J=4.7Hz, 2H) |
| 15 | CH | N | CH | Ph | 105–107° C. | 2944, 1585, 1548, 1500, 1447, 1360, 983 (KBr) | DMSO-d₆ | 1.45(m, 2H); 1.73(m, 2H); 2.21–2.45(c.a. 6H); 3.60–3.75 (c.a. 4H); 4.03(t, J=6.8Hz, 2H) 6.47(t, J=4.7Hz, 1H); 7.21–7.79 (c.a. 7H); 8.25(d, J=4.7Hz, 2H) |
| 16 | CH | N | C—CH=CH—CH= | | 85–88° C. | 2944, 1581, 1542, 1488, 1466, 1355, 1259, 741 (KBr) | DMSO-d₆ | 1.40(m, 2H); 1.82(m, 2H); 2.26–2.42(c.a. 6H); 3.62–3.71 (c.a. 4H); 4.24(t, J=6.9Hz, 2H) 6.56(t, J=4.7Hz, 1H); 7.16–7.26 (c.a. 2H); 7.55–7.70(c.a. 2H); 8.22–8.34(c.a. 3H) |
| 17 | CH | N | C—N=CH—CH= | | 104° C. | 2935, 1578, 1545, 1482, 1443, 1409, 1357, 1256, 982, 751(KBr) | DMSO-d₆ | 1.45(m, 2H); 1.90(m, 2H); 2.23–2.50(c.a. 6H); 3.6 (t, J=4.8Hz, 4H); 4.3(t, J=7.0Hz, 2H); 6.5 (t, J=4.7Hz, 1H); 7.25(d.d, J=4.7Hz, 1H); 8.05 (d, J=7.9Hz, 1H); 8.30–8.48(c.a. 4H) |
| 18 | CH | N | C—CH=CH—N= | | 134° C. | 2944, 2828, 1609, 1582, 1543, 1487, 1460, 1355, 1260, 982, 800 (KBr) | DMSO-d₆ | 1.42(m, 2H); 1.84(m, 2H); 2.28–2.49(c.a. 6H); 3.60–3.69 (c.a. 4H); 4.03(t, J=7.0Hz, 2H) 6.5(t, J=4.7Hz, 1H); 7.28(d.d, J=4.7Hz, 1H); 8.07 (d, J=7.9Hz, 1H); 8.29–8.50(c.a. 4H) |
| 19 | N | N | C—CH=CH—CH= | | 89–90.5° C. | 2940, 2818, 1590, 1544, 1498, 1360, 1259, 984, 749 (KBr) | DMSO-d₆ | 1.43(m, 2H); 1.97(m, 2H); 2.24–2.53(c.a. 6H); 3.66 (t, J=5.1Hz, 4H); 4.75(t, J=6.8Hz, 2H); 6.60 (t, J=4.7Hz, 1H); 7.52(m, 2H); 8.01(m, 2H); 8.31(s, 1H); 8.36(s, 1H) |
| 20 | CCl | N | C—CH=CH—CH= | | 153–145° C. | 2940, 1583, 1542, 1491, 1466, 1443, 1383, 1264, 1128, 981, 742 (KBr) | DMSO-d₆ | 1.50(m, 2H); 1.81(m, 2H); 2.20–2.42(c.a. 6H); 3.67 (m, 4H); 4.28(t, J=7Hz, 2H); 6.58(t, J=4.7Hz, 1H); 7.30 (m, 2H); 7.60(m, 2H); 8.31(d, J=4.7Hz, 2H) |

| Example | Z₁ | Z₂ | R₃ | Z₄ | m.p. | IR cm⁻¹ | NMR solvent | ¹H-NMR(100 MHz), δ = Hz |
|---|---|---|---|---|---|---|---|---|
| 21 | CH | N | Cl–C–CH=CH–C=CH– | N | 82–84° C. | 2945, 1583, 1544, 1492, 1356, 1260, 983, 799 (KBr) | CDCl₃ | 1.55(m, 2H); 1.94(m, 2H); 2.30–2.48(c.a. 6H); 3.75–3.85 (c.a. 4H); 4.16(t, J=7Hz, 2H); 6.45(t, J=4.7Hz, 1H); 7.27 (s, 1H); 7.34(dd, J=9Hz, J'=2Hz, 1H); 7.70(d, J=9Hz); 7.87(d, J=4.7Hz, 1H); 8.27(d, J=4.7Hz, 2H) |
| 22 | CH | N | Cl–C–CH=C–CH=CH– | N | 91–93° C. | 2945, 1585, 1543, 1490, 1350, 1260, 983, 799 (KBr) | CDCl₃ | 1.55(m, 2H); 1.94(m, 2H); 2.30–2.48(c.a. 6H); 3.75–3.85 (c.a. 4H); 4.16(t, J=7Hz, 2H); 6.45(t, J=4.7Hz, 1H); 7.16 (dd, J=9Hz, J'=2Hz, 1H); 7.27(s, 1H); 7.83(d, J=9Hz, 1H); 7.87(d, J=2Hz, 1H); 8.27 (d, J=4.7Hz, 2H) |
| 23 | CH | N | H | N | 69–71° C. | 2942, 1582, 1546, 1458, | CDCl₃ | 1.55(m, 2H); 1.96(m, 2H); 2.32–2.51(c.a. 6H); 3.81(t, J=5.1Hz, 4H); |

TABLE I-continued
| | | | | | |
|---|---|---|---|---|---|
| 24 | N | —CH=CH—CH=CH— | 97.4-98.2° C. | 1448, 1360, 1261, 1138, 1011, 983, 680 (KBr) 2946, 2863, 2823, 1585, 1547, 1483, 1358, 1256, 982, 799, 761 (KBr) | DMSO-d6 | 4.21(t, J=7.0Hz, 2H); 6.4(t, J=4.7Hz, 1H); 7.95(s, 1H); 8.09(s, 1H); 8.29(d, J=4.7Hz, 2H) 1.34-1.56(m, 2H); 1.37-2.23(m, 2H); 2.18-2.48(c.a. 6H); 3.56(t, J=5.3Hz, 4H); 4.75(t, J=6.8Hz, 2H); 6.56 (t, J=4.7Hz, 1H); 7.40(dd, J=6.5Hz, J'=3.1Hz, 2H); 7.90(dd, J=6.6Hz, J'=3.3Hz, 2H); 8.28(s, 1H); 8.33(s, 1H) |
| 25 | CMe | C—CH=CH—CH=CH— | 101-102° C. | 2938, 2820, 1583, 1542, 1494, 1405, 1357, 1258, 983, 798, 744 (KBr) | CDCl3 | 1.56-1.93(c.a. 4H); 2.30-2.47(c.a. 6H); 2.58(s, 3H); 3.79 (t, J=5.2Hz, 4H); 4.10(t, J=7.3Hz, 2H); 6.43(t, J=4.7Hz, 1H); 7.22(m, 3H); 7.67(m, 1H); 8.26(d, J=4.7Hz, 2H) |
| 26 | CH | CH3 CH3<br>   \|      \|<br>C—CH=C——C=CH— | 105-106° C. | 2946, 1584, 1542, 1491, 1466, 1362, 1262, 983, 800, 742 (KBr) | CDCl3 | 1.50(m, 2H); 1.85(m, 2H); 2.25-2.43(c.a. 12H); 3.76 (t, J=5.0Hz, 4H); 4.07(t, J=7.0Hz, 2H); 6.40 (t, J=4.7Hz, 1H); 7.11(s, 1H); 7.51(s, 1H); 7.71(s, 1H); 8.23(d, J=4.7Hz, 2H) |

TABLE II

| Example | $Z_1$ | $Z_2$ | $R_3$ | $Z_4$ | $R_7$ | $R_8$ | $R_9$ | m.p. | IR cm$^{-1}$ | NMR solvent | $^1$H-NMR(100 MHz), δ, J=Hz |
|---|---|---|---|---|---|---|---|---|---|---|---|
| 27 | N | CH | Cl | CH | H | H | MeO— | 76-77° C. | 2833, 1511, 1448, 1247, 1029, 979, 824 (KBr) | DMSO-d$_6$ | 1.43(m, 2H); 1.78(m, 2H); 1.71-2.48(c.a. 6H); 2.93-3.02 (m, 4H); 3.67(s, 3H); 4.09 t, J=6.8Hz, 2H); 6.83(s, 4H); 7.52(s, 1H); 7.98(s, 1H) |
| 28 | CMe | N | Cl | CCl | H | H | MeO— | 73-75° C. | 2940, 2818, 1512, 1457, 1245, 1183, 1036, 826 (KBr) | DMSO-d$_6$ | 1.33-1.87(c.a. 4H); 2.32(s, 3H); 2.41-2.51(c.a. 6H); 2.82-3.0(m, 4H); 3.67(s, 3H); 3.93(t, J=7.2Hz, 2H); 6.83(s, 4H); |
| 29 | CH | Cl | CH | MeO— | H | H | Oil | | 2941, 2816, 1500, 1450, 1241, 749, (film) | DMSO-d$_6$ | 1.39(m, 2H); 1.77(m,2H); 2.22-2.45(c.a. 6H); 2.92 (m, 4H); 3.76(s, 3H); 4.07(t, J=6.0Hz, 2H); 6.87(m, 4H); 7.51(s,1H); 7.95(s, 1H) |
| 30 | CMe | N | Cl | CCl | MeO— | H | H | 82-83° C. | 2943, 2820, 1502, 1405 1241, 1030, 746 (KBr) | DMSO-d$_6$ | 14.43-1.60(c.a. 4H); 2.33)m, 3H); 2.40-2.50(c.a. 6H); 3.95(m, 4H); 3.76(s, 3H); 3.93(t, J=7.0Hz, 2H); 6.89 (m, 4H) |
| 31 | N | CH | Cl | CH | H | MeO— | H | Oil | 2943, 2820, 1601, 1578 1496, 1451, 1203, 1171 970 (film) | CDCl$_3$ | 1.52(m, 2H); 1.85(m, 2H); 2.28-2.56(c.a. 6H); 3.16(m, 4H); 3.7(s, 3H); 4.05(t, J=7.0Hz, 2H); 6.4(m, 3H); 7.15(m, 1H); 7.34(s, 1H); 7.40(s, 1H) |
| 32 | CH | H | CH | H | H | MeO— | oil | | 2943, 2815, 1512, 1455, 1244, 1037, 823, 724 (film) | CDCl$_3$ | 1.50-1.80(c.a. 4H); 2.31-2.61(c.a. 6H); 3.06(m, 4H); 3.16(m, 2H); 6.6(m, 2H); 6.84(s,4H) 3.81(t, J=7.0Hz, 2H); 6.1(m, 2H); |
| 33 | CH | H | CH | MeO— | H | H | oil | | 2940, 2814, 1500, 1451, 1281, 1241, 1028, 743, 723 (film) | CDCl$_3$ | 1.50-1.85(c.a. 4H); 2.33-2.66(c.a. 6H); 3.10(m, 4H); 3.84-3.96(c.a. 5H); 6.12(t, J=2Hz, 2H); 6.45(t, J=2Hz, 2H); 6.93(m, 4H) |
| 34 | CH | H | CH | H | H | H | oil | | 2946, 2817, 1600, 1501, 1235, 759, 723, 692 (film) | CDCl$_3$ | 1.41-1.89(c.a. 4H); 2.37(t, J=7.3Hz, 2H); 2.50-2.60 (c.a. 4H); 3.18(m, 4H); 3.89(t, J=6.9Hz, 2H); 6.13(t, J=2.0Hz, 2H); 6.64(t, J=2.0Hz, 2H); 6.83-7.33 (c.a. 5H) |
| 35 | N | CH | Cl | CH | H | H | H | 58-61° C. | 2942, 2819, 1600, 1500, 1450, 1381, 1311, 1240, 1140, 966, 756 (KBr) | CDCl$_3$ | 1.47(m, 2H); 1.84(m, 2H); 2.35(t, J=7.2Hz, 2H); 2.52(m, 4H); 3.16(m, 4H); 4.04(t, J=6.8Hz, 2H); 6.75-6.94 (c.a. 3H); 7.16(s, 1H); 7.23(s, 1H); 7.35(d, J=7.4Hz, 2H) |
| 36 | CMe | N | Cl | CH | H | H | H | oil | 2944, 2819, 1600, 1532 1503, 1453, 1404, 1244, 1143, 759, 692 (film) | CDCl$_3$ | 1.43-1.87(c.a. 4H); 2.33(s, 3H); 2.38-2.60(c.a. 6H) 3.17(m, 4H); 3.83(t, J=2Hz, 2H); 6.9(c.a. 3H); 7.24(m, 2H) |
| 37 | N | CH | Cl | CCl | H | H | H | oil | 2943, 2817, 1587, 1480, 1443, 1231, 1040, 971, 751, 612 (film) | DMSO-d$_6$ | 1.40(m, 2H); 1.78(m, 2H); 2.2-2.6(c.a. 6H); 2.95(m, 4H); 4.08(t, J=6.3Hz, 2H); 6.95-7.41(c.a. 4H); 7.50(s, 1H); 7.97(s, 1H) |
| 38 | CMe | N | Cl | CCl | Cl | H | H | 89-91° C. | 2936, 2818, 1587, 1531, 1480, 1359, 1243, 1229, 1036, 1016 (KBr) | CDCl$_3$ | 1.3-1.8(c.a. 4H); 2.33(s,3H); 2.35-2.70(c.a. 6H); 2.96 (m, 4H); 3.94(t, J=7.2Hz, 2H); 6.90-7.50(c.a. 4H) |
| 39 | N | CH | Cl | CH | H | Cl | H | oil | 2944, 2820, 1594, 1564, 1487, 1451, 1433, 1384, 1239, 987, 980 (film) | CDCl$_3$ | 1.3-1.70(m, 2H); 1.70-2.10(m, 2H); 2.39(T, J=7.4Hz, 2H); 2.59(m, 4H); 3.17(m, 4H); 4.09(t, J=7.4Hz, 2H); 6.7-6.9(c.a. 3H); 7.15(t, J=8.0Hz, 1H); 7.37(s, 1H); 7.4(s, 1H) |

TABLE III $$\text{Ar}-N\underset{}{\overset{}{\bigcirc}}N-(CH_2)_n-Z_6-Z_5\underset{Z_1}{\overset{Z_4}{\bigcirc}}\overset{R_3}{\underset{Z_2}{\bigcirc}}\cdot X$$

| Example | $Z_1$ | $Z_2$ | $Z_4$ | $Z_5$ | $Z_6$ | $R_3$ | n | X | Ar | m.p. | IR cm$^{-1}$ | NMR solvent | $^1$H-NMR (100 MHz), δ, J=Hz |
|---|---|---|---|---|---|---|---|---|---|---|---|---|---|
| 40 | N | CH | CH | N | CH$_2$ | H | 3 | — | 2-methyl-1-methylpyrrole | oil | 2943, 2812, 1525, 1509, 1469, 1455, 1282, 1137, 751 (film) | CDCl$_3$ | 1.52(m, 2H); 1.91(m, 2H); 2.30–2.60(c.a. 6H); 3.08(m, 4H); 4.15(t, J=7Hz, 2H); 6.22(t, J=2Hz, 1H); 6.64(d, J=1.4Hz, 1H); 6.76(d, J=1.4Hz, 1H); 7.38(d, J=2Hz, 1H); 7.48 (d, J=2Hz, 1H) |
| 41 | N | CH | CH | N | CH$_2$ | Cl | 1 | — | 2-methoxyphenyl | oil | 2942, 2819, 1594, 1500, 1450, 1241, 1036, 971, 750 (film) | CDCl$_3$ | 2.70–2.73 (c.a. 4H); 2.87(t, J=6.5Hz, 2H); 3.05–3.10 (c.a. 4H); 3.86(s, 3H); 4.25(t, J=6.5Hz, 2H); 6.85–7.1 (c.a. 4H); 7.41(s, 1H); 7.52(s, 1H) |
| 42 | CMe | N | CCl | N | CH$_2$ | Cl | 3 | citrate | 2-methylpyrazine | 137–138° C. | 1713, 1618, 1590, 1552, 1511, 1436, 1372, 1247, 1214 (KBr) | DMSO-d$_6$ | 1.51–1.71(c.a. 4H); 2.32(s, 3H); 2.64–2.74(c.a. 10H); 3.72–3.98(c.a. 6H); 6.64(t, J=4.6Hz, 1H); 8.36 (d, J=4.6Hz, 2H); 9.75(c.a. 4H) |
| 43 | N | CH | CH | N | CH$_2$ | Cl | 3 | — | 3-methylindazole | oil | 2943, 2815, 1493, 1451, 1423, 1383, 1307, 1261, 970, 739, 613 (film) | CDCl$_3$ | 150(m, 2H); 1.85(m, 2H); 2.45(t, J=7.2Hz, 2H); 2.60(t, J=4.7Hz, 4H); 3.53(t, J=5.0Hz, 4H); 4.07(t, J=7.0Hz, 4H); 7.35(m, 4H); 7.85(m, 2H) |
| 44 | CMe | N | CCl | N | CH$_2$ | Cl | 3 | — | 3-methylbenzisothiazole | oil | 2944, 2816, 1533, 1493, 1422, 1380, 1280, 1246, 1139, 1017, 754, 665 (film) | CDCl$_3$ | 1.55–1.85(c.a. 4H); 2.34–2.49(c.a. 5H); 2.62(t, J=4.7Hz, 4H); 3.53(t, J=5.0Hz, 4H); 3.84(t, J=7.0Hz, 2H); 7.37(m, 2H); 7.83(m, 2H) |
| 45 | NMe | N | CH | C | NH | CH$_3$ | 3 | — | 2-methoxyphenyl | oil | 3230, 2942, 2819, 1570, 1500, 1450, 1241, 750 (film) | CDCl$_3$ | 1.77(m, 2H); 2.11(s, 3H); 2.34–2.63(c.a. 6H); 3.05–3.15 (c.a. 6H); 3.54(s, 3H); 3.84(s, 3H) 4.97(broad, 1H); 5.21(s, 1H); 6.91(m, 4H) |

BIOLOGICAL ACTIVITY

ANXIOLYTIC AND/OR TRANQUILLISING ACTIVITY

For a few examples the activity on the central nervous system, and more precisely their anxiolytic and tranquillising activity, is demonstrated by means of the conditioned avoidance response test using the method of J. S. New et al. (J. S. New, J. P. Yevich, M. S. Eison, D. P. Taylor, A. S. Eison, L. A. Riblet, C. P. Van der Maelen, D. L. Temple, *J.Med.Chem.* 1986, 29, 1476).

Male Wistar rats weighing 200 grammes which have been trained to jump over a barrier in an avoidance and escape cage (shuttle box) (Letica, reference LI 910 and LI 2700) within 30 seconds of their being introduced into the cage are used in this test.

The products having an anxiolytic or tranquillising activity suppress the conditioned avoidance response.

Training: day one: 11 trials at 3 minute intervals. Electric shock to the paws after 30 seconds (5 mA, 0.1 s, 10 s).

Days two and three: 2 trials per day, with the selected rats only (sum of the scores for the first day (with the exception of the first trial) >14).

Test day: groups formed by selected rats. Oral administration of the product or the vehicle 45 minutes before the start of the study.

The results obtained for a few products are summarized in Table IV.

Taking account of their pharmacodynamic properties, 1-{4-[4-(2-aryl(or heteroaryl)-1-piperazinyl]-butyl}-1H-azole derivatives according to the invention may be used satisfactorily in human and veterinary medicine, in particular in the treatment of disorders of the central nervous system and more particularly for the treatment of anxiety or as tranquillisers.

In human medicine, the administration dose of course depends on the severity of the disease. It will generally be between about 5 and about 100 mg/day. The derivatives of the invention will, for example, be administered in the form of tablets, solutions or suspensions or capsules.

TABLE IV

| | INHIBITION OF THE CONDITIONED AVOIDANCE RESPONSE | |
|---|---|---|
| Example | Activity % (D = 80 mg/kg, p.o.) | $ED_{50}$ (mg/kg, p.o.) |
| 1 | 94 | 32.4 |
| 2 | 37 | — |
| 3 | 74 | 42.8 |
| 4 | 30 | — |
| 5 | 68 | 33.5 |
| 6 | 57 | 44.3 |
| 7 | 74 | 29.0 |
| 8 | 29 | — |
| 9 | 8 | — |
| 10 | 38 | — |
| 11 | 82 | 24.5 |
| 12 | 46 | — |
| 13 | 70 | 17.1 |
| 14 | 38 | — |
| 15 | 73 | 28.0 |
| 16 | 100 | 6.1 |
| 17 | 86 | 21.9 |
| 18 | 91 | 25.6 |
| 19 | 99 | — |
| 20 | 77 | 15.4 |

TABLE IV-continued

| | INHIBITION OF THE CONDITIONED AVOIDANCE RESPONSE | |
|---|---|---|
| Example | Activity % (D = 80 mg/kg, p.o.) | $ED_{50}$ (mg/kg, p.o.) |
| 21 | 100 | 9.3 |
| 22 | 100 | 9.1 |
| 23 | 100 | 6.3 |
| 24 | 87 | — |
| 25 | 52 | 61.7 |
| 26 | 88 | 34.5 |
| 27 | 88 | — |
| 28 | 75 | 37.5 |
| 29 | 100 | 8.9 |
| 30 | 95 | 12.8 |
| 31 | 100 | 20.8 |
| 32 | 83 | 50 |
| 33 | 99 | 23.9 |
| 34 | 96 | 23.7 |
| 35 | 100 | 20.7 |
| 36 | 76 | 42 |
| 37 | 86 | 29.5 |
| 38 | 78 | — |
| 39 | 100 | — |
| 40 | 28 | — |
| 41 | 52 | — |
| 42 | 82 | 24.5 |
| 43 | 100 | — |
| 44 | 95 | — |
| 45 | 100 | — |
| Buspirone | 99 | 17.2 |
| Ipsapirone | 98 | 26.1 |

INHIBITION OF THE ABSTINENCE SYNDROME

The light box/dark box test described by B. Costall et al. (*J. Phar. Pharmacol.*, 1988, 40: 494–500) is used. The mouse is placed in the light zone of a box divided into two compartments, one brightly illuminated, the light box, and the other with little illumination, the dark box.

1) The number of times the mouse stands up on the hind paws in each compartment during a 5 minute period is counted (see Column 1 of Table V).

2) The activity in each compartment is given by counting the number of crossings through the squares which form the divisions of each compartment (see Column 2 of Table V).

3) The time passed in the dark box during the 5 minute counting period is determined (see Column 3 of Table 5).

4) The initial latent period is determined, that is to say the time which elapses after the animal is placed in the light box, at the start of the test, before it enters the dark box (see Column 4 of Table 5). The anxiolytic or anxiogenic behaviour of the mice is determined in the course of different periods of treatment and in each case is compared with that of a group of control animals which have not been given any treatment.

Treatments And Experimental Set-Up

1) Dependency on a given treatment (diazepam, cocaine, alcohol or nicotine) employing daily administration over a period of 7 or 14 days. This treatment causes an anxiolytic response (the activity and the time present in the light box increase).

Dosages:

Diazepam: 10 mg/kg i.p. twice per day over a period of 7 days.
Cocaine: 1 mg/kg i.p. over a period of 14 days.
Alcohol: Administered at 8% weight/volume in the drinking water over a period of 14 days.
Nicotine: 0.1 mg/kg i.p. twice per day over a period of 7 days.

2) Cessation of the treatment, which within 24 hours gives rise to an abstinence syndrome which manifests itself as an anxiogenic response (increases the activity and the presence in the dark box).

3) Other different groups receive, in addition to diazepam, cocaine, alcohol or nicotine, a concomitant treatment with products which are the subject of the present invention and, by way of comparison, with buspirone or ipsapirone. The diazepam, cocaine, alcohol or nicotine treatment is also withdrawn from these groups and the response at the end of 24 hours is also observed.

The product described and the doses tested were:
4,5-dichloro-2-methyl-1-{4-[4-(2-pyrimidinyl)-1-piperazinyl]-butyl}-1H-imidazole citrate.

(Example 42): 1 μg/kg p.o. twice per day.

The results observed have been given in the following Tables (V).

The responses obtained with the product which is the subject of the present invention were as follows:

The derivative of Example 42 inhibits the abstinence syndrome, which manifests itself as an anxiogenic response, induced by diazepam, cocaine, alcohol and nicotine, and in addition it maintains a significant anxiolytic response when the administration of diazepam, cocaine, alcohol or nicotine is stopped.

Buspirone maintains the abstinence syndrome, which manifests itself by an anxiogenic response, induced by diazepam and cocaine. However, when the treatment with alcohol and nicotine is stopped, an abstinence syndrome, i.e. anxiogenesis, no longer exists. Buspirone significantly inhibits only a few anxiogenic response parameters after the treatment with alcohol is stopped.

Ipsapirone maintains the abstinence syndrome, which manifests itself by an anxiogenic response, induced by diazepam, cocaine and nicotine. Ipsapirone inhibits the abstinence syndrome, which manifests itself in the form of an anxiogenic response induced by alcohol.

TABLE V

| TREATMENT | NUMBER OF TIMES STANDING ERECT WITHIN 5 MIN. PERIOD L-D | ACTIVITY WITHIN 5 MIN. PERIOD L-D | TIME IN BOX D | LAT. L-D |
|---|---|---|---|---|
| EFFECT OF A LONG-TERM TREATMENT WITH COCAINE AND STOPPING, INHIBITION OF THE ABSTINENCE SYNDROME WITH THE PRODUCT CORRESPONDING TO EXAMPLE 42 | | | | |
| Control | 25   87 | 30   94 | 60 | 10 |
| Cocaine | 60*   38* | 68*   30* | 30* | 18* |
| Coca. + stopping 24 h | 7+   122+ | 10+   149+ | 83+ | 2+ |
| Coca. + stopping 24 h + Ex. 42 | 86o*   20o* | 92o*   23o* | 30o* | 26o* |
| Coca. + stopping 24 h + Buspirone | 10+   98+ | 18+   90+ | 70+ | 2+ |
| Coca. + stopping 24 h + Ipsapirone | 11+   89+ | 18+   85+ | 62+ | 8+ |
| EFFECT OF A LONG-TERM TREATMENT WITH DIAZEPAM AND STOPPING, INHIBITION OF THE ABSTINENCE SYNDROME WITH THE PRODUCT CORRESPONDING TO EXAMPLE 42 | | | | |
| Control | 22   83 | 36   93 | 58 | 12 |
| Diazepam | 70*   25* | 73*   24* | 25* | 27* |
| Diaz. + stopping 24 h | 5+   146+ | 5+   164+ | 80+ | 1.8   24 |
| Diaz. + stopping 24 h + Ex. 42 | 85o*   17o* | 96o*   19o* | 36o* | 28o* |
| Diaz. + stopping 24 h + Buspirone | 9+   88+ | 12+   100+ | 72+ | 2+ |
| Diaz. stopping 24 h + Ipsapirone | 15+   82+ | 17+   88+ | 90+ | 8+ |
| EFFECT OF A LONG-TERM TREATMENT WITH ALCOHOL AND STOPPING, INHIBITION OF THE ABSTINENCE SYNDROME WITH THE PRODUCT CORRESPONDING TO EXAMPLE 42 | | | | |
| Control | 22   94 | 30   102 | 59 | 11 |

TABLE V-continued

| TREATMENT | NUMBER OF TIMES STANDING ERECT WITHIN 5 MIN. PERIOD L-D | | ACTIVITY WITHIN 5 MIN. PERIOD L-D | | TIME IN BOX D | LAT. L-D |
|---|---|---|---|---|---|---|
| Alcohol | 72* | 22* | 80* | 28* | 28* | 28* |
| Alcohol + stopping 24 h | 5+ | 147+ | 6+ | 167+ | 84+ | 2+ |
| Alcohol + stopping 24 h + Ex. 42 | 86o* | 17o* | 97o* | 23o* | 26o* | 20o* |
| Alcohol + stopping 24 h + Buspirone | 18o | 80o | 15 | 75o | 62 | 7 |
| Alcohol + stopping 24 h + Ipsapirone | 21o | 75o | 36o | 80o | 35o | 10o |
| EFFECT OF A LONG-TERM TREATMENT WITH NICOTINE AND STOPPING, INHIBITION OF THE ABSTINENCE SYNDROME WITH THE PRODUCT CORRESPONDING TO EXAMPLE 42 | | | | | | |
| Control | 22 | 83 | 36 | 93 | 58 | 12 |
| Nicotine | 66* | 23* | 70* | 25* | 25* | 26* |
| Nic. + stopping 24 h | 10+ | 125+ | 14+ | 147+ | 78+ | 2+ |
| Nic. + stopping 24 h + Ex. 42 | 90o* | 18o* | 102o* | 20o* | 29o* | 23o* |
| Nic. + stopping 24 h + Buspirone | 12 | 80 | 20 | 85 | 65 | 8 |
| Nic. + stopping 24 h + Ipsapirone | 9o | 84o | 18o | 98o | 70o | 3o |

*p 0.001 (anxiolysis)
+: p 0.001 (anxiogenesis)
o: p 0.001 (reversion of anxiogenesis)
L-D: Light-dark The derivatives of general formula I according to the invention are therefore useful as active substances in medicaments intended for the treatment of disorders associated with the abstinence syndrome, which manifests itself in particular in the form of an anxiogenic response, induced by the sudden suppression of a long-term treatment with benzodiazapines such as diazepam, cocaine, alcohol and/or nicotine.

In human medicine, the administration dose of course depends on the severity of the syndrome.

It will generally be between about 5 and about 100 mg/day.

ANTIHYPERTENSIVE ACTIVITY

For a few examples the activity on the cardiovascular system, in particular their antihypertensive activity, is demonstrated. This activity is manifested by the protection of animals before death induced by an intravenous injection of norepinephrine, which produces a hypertensive attack in rats.

Norepinephrine Antagonism Test In Rats

The antihypertensive activity is demonstrated by means of the test described by P. A. J. Janssen et al. (P. A. J. Janssen, C. J. E. Niemegeers, K. H. L. Schellekens, F. J. Verbruggen and J. M. Van Nueten, Arzneim, Forsch., 1963, 13, 205).

Male Wistar rats weighing 200 grammes are used in this test. The product to be studied is administered intraperitoneally and 1.25 mg/kg (i.v.) of norepinephrine are administered after 2 hours. This treatment causes the death of the control animals.

The initial administration dose in these studies is 40 mg/kg (i.p.).

The $ED_{50}$ of the most active products is determined and the results obtained are summarized in Table VI.

TABLE VI

| | NOREPINEPHRINE ANTAGONISTIC ANTIHYPERTENSIVE ACTIVITY | |
|---|---|---|
| Example | Activity % (D = 40 mg/kg, p.o.) | $ED_{50}$ (mg/kg, p.o.) |
| 1 | 0 | — |
| 2 | 0 | — |
| 3 | 25 | — |
| 4 | 0 | — |
| 5 | 0 | — |
| 6 | 75 | 31.7 |
| 7 | 0 | — |
| 8 | 0 | — |
| 9 | 0 | — |
| 10 | 0 | — |
| 11 | 0 | — |
| 12 | 0 | — |
| 13 | 0 | — |

TABLE VI-continued

| | NOREPINEPHRINE ANTAGONISTIC ANTIHYPERTENSIVE ACTIVITY | |
|---|---|---|
| Example | Activity % (D = 40 mg/kg, p.o.) | ED$_{50}$ (mg/kg, p.o.) |
| 14 | 0 | — |
| 15 | 0 | — |
| 16 | 0 | — |
| 17 | 0 | — |
| 18 | 100 | 3.97 |
| 19 | 0 | — |
| 20 | 0 | — |
| 21 | 0 | — |
| 22 | 0 | — |
| 23 | 50 | — |
| 24 | 50 | — |
| 25 | 25 | — |
| 26 | 0 | — |
| 27 | 0 | — |
| 28 | 100 | 14 |
| 29 | 100 | 0.46 |
| 30 | 100 | 0.18 |
| 31 | 100 | 8.9 |
| 32 | 0 | — |
| 33 | 100 | 2.23 |
| 34 | 100 | 10 |
| 35 | 100 | 4.1 |
| 36 | 100 | 7.6 |
| 37 | 100 | 1.9 |
| 38 | 100 | 1.3 |
| 39 | 0 | — |
| 40 | 0 | — |
| 41 | 75 | 5 |
| 42 | 0 | — |
| 43 | 66 | — |
| 44 | 100 | — |
| 45 | 100 | 2.8 |
| Clonidine | 100 | 1.58 |
| Tolazoline | 100 | 2.97 |

ACTIVITY WITH RESPECT TO THE IMPROVEMENT OF COGNITION

The activity in respect of the improvement in cognition is demonstrated for Example 42:

The influence of this product on the familiarization process of mice in the light box/dark box test described by J. M. Barnes et al., (Pharmacol. Biochem. Behav., 1990, 35, 955-962) is studied. On the one hand, the effect on learning (the speed of familiarization) and on the other hand the capacity for blocking contrary effects produced by escopolamine are studied.

The mouse is placed in the light zone of a box divided into two compartments, one brightly illuminated, the light box, and the other with little illumination, the dark box.

1) The number of times the mouse stands up on the hind paws in each compartment during a 5 minute period is counted (see Column 1 of the table below).

2) The activity in each compartment is given by counting the number of crossings through the squares which form the divisions of each compartment (see Column 2 of the table below).

3) The time passed in the dark box during the 5 minute counting period is determined (see Column 3 of the table below).

4) The initial latent period is determined, that is to say the time which elapses after the animal is placed in the light box, at the start of the test, before it enters the dark box (see Column 4 of the table below).

Two treatments with the vehicle are administered to the control animals per day. Two doses of 0.00001 ng/kg p.o. of compound 42 are administered per day to the animals treated with this product. The same operation is repeated daily for 5 days.

The animals learn to remain in the dark box for a longer period and to go into the box more rapidly.

On day six escopolamine (2×0.25 mg/kg, i.p.) is administered. With this treatment the animals of the control group "forget" the learned behaviour comprising remaining in the dark box for a longer period.

They recover the learned habit on day seven.

The treatment with a product which improves cognition has the following effects:

1) The behaviour learned is improved, learning is more rapid and the residence time in the dark box increases.

2) The learning reversal produced by escopolamine is completely blocked.

The data obtained are summarized in Table VII. They demonstrate that compound 42 has a cognition-improving activity, given that this compound improves the learning process and blocks the effects of escopolamine.

Piracetam tested under the same conditions has no activity.

TABLE VII

| | INFLUENCE OF EXAMPLE 42 (0.00001 ng/kg, p.o., TWICE PER DAY) ON THE FAMILIARISATION PROCESS IN MICE, DETERMINED BY THE LIGHT BOX/DARK BOX TEST. | | | | | | | |
|---|---|---|---|---|---|---|---|---|
| | NO. OF TIMES STANDING ERECT WITHIN 5 MIN. PERIOD | | ACTIVITY WITHIN 5 MIN. PERIOD | | TIME IN THE BOX | | LATENT PERIOD | |
| TREATMENT DAY | CONTROL L-D | EXAMPLE 42 L-D | CONTROL L-D | EXAMPLE 42 L-D | CONTROL D | EXAMPLE 42 D | CONTROL L-D | EXAMPLE 42 L-D |
| 1 | 22   72 | 23   79 | 34   79 | 36   82 | 60 | 60 | 11 | 11 |
| 2 | 26   76 | 10*  147* | 36   83 | 11*  167* | 61 | 80* | 12 | 2* |
| 3 | 24   74 | 8*   156* | 34   78 | 10*  179* | 60 | 79* | 11 | 2* |
| 4 | 9*   147* | 9*   161* | 12*  167* | 9*   183* | 80* | 83* | 2* | 1.5* |
| 5 | 9*   138* | 11*  151* | 12*  171* | 12*  176* | 79* | 82* | 2.5* | 1* |
| 6(*) | 59+  38+ | 10*o 172*o | 67+  30+ | 14*o 181*o | 27+ | 81*o | 21+ | 1.5*o |
| 7 | 8*   154* | 8*   181* | 13*  163* | 8*   187* | 81* | 83* | 2.5* | 1* |

(*) 2 preliminary treatments with escopolamine (0.25 mg/kg, i.p.)
*p < 0.001 (improvement in learning, compared with day 1)
+ p < 0.001 (reversal of the familiarisation process produced by escopolamine)
o p < 0.001 (inhibition of the effect of escopolamine)
L-D: Light-dark

ANTIDEPRESSANT ACTIVITY

The antidepressant activity is demonstrated for Example 42. The desperate behaviour test in mice, described by R. D. Porsolt et al. (Arch. Int. Pharmacodyn. 1977, 229, 327-336), is used.

The animals are placed for 6 minutes in a cylinder containing water, from which they are not able to escape. The period of immobility between minutes 2 and 5 is determined for groups of 10 mice per dosage tested.

The product studied is administered i.p. 1 hour before the test. In this test the immobility of the animals is explained as being produced by their depressed state resulting from being faced with an adverse and insoluble situation in a hostile environment such as water.

Antidepressants reduce this immobility.

In our test imipramine (30 mg/kg, i.p.) was used as reference product.

The results demonstrate that compound 42 has an antidepressant activity since it significantly reduces the period of immobility of the control group.

| Product | Doses (mg/kg, i.p.) | Period of immobility (seconds) |
|---|---|---|
| Control | — | 118 |
| Example 42 | 1 | 64 ($p < 0.05$) |
| Imipramine | 30 | 71 ($p < 0.05$) |

Two particular pharmaceutical dosage forms of the derivatives which are the subject of the present invention will be indicated below by way of examples.

| Example of tablet formulation | |
|---|---|
| Compound 42 | 5 mg |
| Lactose | 60 mg |
| Microcrystalline cellulose | 25 mg |
| Povidone | 5 mg |
| Pregelatinised starch | 3 mg |
| Colloidal silica | 1 mg |
| Magnesium stearate | 1 mg |
| Weight of tablet | 100 mg |
| Example of a capsule formulation | |
| Compound 42 | 10 mg |
| Polyoxyethylenated glyceride | 135 mg |
| Glycerol behenate | 5 mg |
| Excipient: soft gelatin q.s. | 150 mg |

We claim:

1. A heterocyclic compound characterized in that it has the formula I

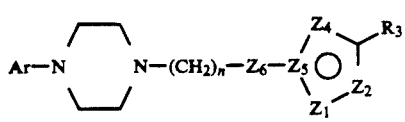

in which
n may have values 1 to 6,
Ar represents an aromatic radical selected from the group consisting of phenyl, phenyl substituted with a methoxy or a halogen atom, a 3-(1, 2-benzisothiaxole radical) and a 2- N-methyl-imidazole radical,
$Z_1$ represents a nitrogen atom or a C-$R_1$ group,
$Z_2$ represents a nitrogen atom or a C-$R_2$ group,
$Z_4$ represents a nitrogen atom or a C-$R_4$ group,
$Z_5$ represents a nitrogen atom, and
$Z_6$ represents a methylene group
and $R_1$, $R_2$, $R_3$ and $R_4$, which may be identical or different, represent a hydrogen atom, a halogen atom, a lower alkyl radical, a carboxy radical, a carboxomide radical, an alkyl carboxylate radical or a phenyl radical.

2. A heterocyclic compound characterized in that it has the formula I

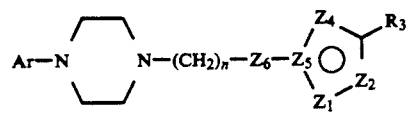

in which
AR represents the 2-pyrimidinyl radical, the five member ring structure together with $R_3$ is imidazopyridine and $Z_6$ represents a nitrogen atom or a carbon atom, each associated with a sufficient number of hydrogen atoms to satisfy its valence.

3. A heterocyclic compound characterized in that it has the formula II

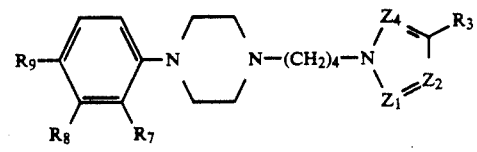

in which $Z_1$ is nitrogen, $Z_2$ is CH, $R_3$ is chlorine, $Z_4$ is CCl, $R_7$ and $R_8$ are hydrogen and $R_9$ is a methoxy group.

4. A heterocyclic compound characterized in that it has the formula II

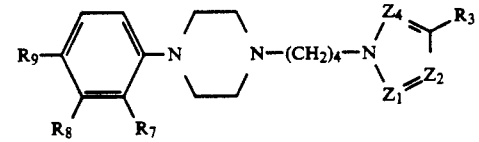

in which $Z_1$ is CMe, $Z_2$ is nitrogen, $R_3$ is chlorine, $Z_4$ is CH, $R_7$ is a methoxy group and $R_8$ and $R_9$ are hydrogen.

5. A compound according to claim 2 wherein $Z_6$ represents an aza group.

6. A heterocyclic compound as claimed in claim 1, wherein Ar represents a 3-(1,2-benzisothiazole) radical.

7. A heterocyclic compound as claimed in claim 1, wherein Ar represents 2-N-methyl-imidazole radical.

8. The compounds selected from the following group:
   - -1-{4-[4-(2-pyrimidinyl)-1-piperazinyl]-butyl}-3H-imidazo[5,4-b]pyridine,
   - -1-{4-[4-(2-pyrimidinyl)-1-piperazinyl]-butyl}-1H-imidazo{4,5-b]pyridine,
   - -2-{4-[4-(2-pyrimidinyl)-1-piperazinyl]-butyl}-2H-benzothiazole,
   - -4-chloro-1-{4-[4-(4-methoxyphenyl)-1-piperazinyl]-butyl}-1H-pyrazole, -4,5-dichloro-2-methyl-1-{4-[4-(4-methoxyphenyl)
 -1-piperazinyl]-butyl}-1H-imidazole,
-4-chloro-1-{4-[4-(2-methoxyphenyl)-1-piperazinyl]-
 butyl}-1H-pyrazole,
-4,5-dichloro-2-methyl-1-{4-[4-(2-methoxyphenyl)
 -1-piperazinyl]-butyl}-1H-imidazole,
-4-chloro-1-{4-[4-(3-methoxyphenyl)-1-piperazinyl]-
 butyl}-1H-pyrazole,
-1-{4-[4-(4-methoxyphenyl)-1-piperazinyl]-butyl}-
 pyrrole,
-1-{4-[4-(2-methoxyphenyl)-1-piperazinyl]-butyl}-
 pyrrole,
-1-{4[(4-phenyl)-1-piperazinyl]-butyl}-pyrrole,
-4-chloro-1-{4-[4-phenyl-1-piperazinyl]-butyl}-1H-
 pyrazole,
-4,5-dichloro-2-methyl-1-{4-[4-phenyl-1-piperazinyl]-
 butyl}-1-H-imidazole,
-4-chloro-1-{4-[4-(2-chlorophenyl)-1-piperazinyl]-
 butyl}-1-H-pyrazole,
-4,5-dichloro-2-methyl-1-{4-[4-(2-chlorophenyl)-1-
 piperazinyl]-butyl}-1H-imidazole,
-4-chloro-1-}4-[4-(3-chlorophenyl)-1-piperazinyl]-
 butyl}-1H-pyrazole,
-1-{4-[4-(2-N-methylimidazole)-1-piperazinyl]-
 butyl}-1H-pyrazole,
-4-chloro-1-{2-[4-(2-methoxyphenyl)-1-piperazinyl]-
 ethyl}-1H-pyrazole,
-4-chloro-1-{4-[4-(3-(1,2-benzisothiazolyl))-1-
 piperazinyl]-butyl}-1H-pyrazole,
-4,5-dichloro-2-methyl-1-{4-[4-(3-(1,2benzisothiazo-
 lyl))-1-piperazinyl]-butyl}-1H-imidazole.

* * * * *

UNITED STATES PATENT AND TRADEMARK OFFICE
CERTIFICATE OF CORRECTION

PATENT NO. : 5,292,739

DATED : March 8, 1994

INVENTOR(S) : Merce-Vidal et al.

It is certified that error appears in the above-indentified patent and that said Letters Patent is hereby corrected as shown below:

Column 6, line 8, delete [imidazor] and insert --imidazo--.

Column 6, line 23, delete [pyrazol] and insert --pyrazole--.

Column 8, line 38, delete [crystallise] and insert --crystalize--.

Columns 9 and 10, Table I, Example 5, Table Column 9 (left to right), line 1, after "1.38(m, 2H):" insert --1.81(m, 2H)--.

Columns 9 and 10, Table I, Example 8, Table Column 7 (left to right), line 3, delete [1307, 1260,] and insert --754, 700--.

UNITED STATES PATENT AND TRADEMARK OFFICE
CERTIFICATE OF CORRECTION

PATENT NO. : 5,292,739  Page 2 of 7
DATED : March 8, 1994
INVENTOR(S) : Merce-Vidal et al.

It is certified that error appears in the above-indentified patent and that said Letters Patent is hereby corrected as shown below:

Columns 9 and 10, Table I, Example 9, Table Column 7 (left to right), delete [2942, 1585, 1307, 1260, 1445, 1360, 1307, 1260, 698 (film)] and insert --2942, 1585, 1546, 1501, 1445, 1360, 1260, 983, 698 (film)--.

Columns 11 and 12, Table I, Example 13, Table Column 7 (left to right), line 2, delete [1547, 1500 ] and insert --1260, 983--.

Columns 11 and 12, Table I, Example 14, Table Column 9 (left to right), line 1, delete [3.67] and insert --3.65--.

UNITED STATES PATENT AND TRADEMARK OFFICE
CERTIFICATE OF CORRECTION

PATENT NO. : 5,292,739
DATED : March 8, 1994
INVENTOR(S) : Merce-Vidal et al.

It is certified that error appears in the above-indentified patent and that said Letters Patent is hereby corrected as shown below:

Columns 13 and 14, Table I, Example 23, Table Column 9 (left to right), line 2, delete [6.4] and insert --6.47--.

Columns 13 and 14, Table I, Example 24, Table Column 9 (left to right), delete [1.37] and insert --1.97--.

Columns 15 and 16, Table II, Example 30, Table Column 9 (left to right), line 1, delete [14.43] and insert --1.43--; same line, delete [2.33)] and insert --2.33(--.

Columns 15 and 16, Table II, Example 30, Table Column 9 (left to right), line 2, delete [3.95] and insert --2.95--.

UNITED STATES PATENT AND TRADEMARK OFFICE
CERTIFICATE OF CORRECTION

PATENT NO. : 5,292,739
DATED : March 8, 1994
INVENTOR(S) : Merce-Vidal et al.

It is certified that error appears in the above-indentified patent and that said Letters Patent is hereby corrected as shown below:

Columns 15 and 16, Table II, Example 33, Table Column 9 (left to right), line 2, delete [6.45] and insert --6.65--.

Columns 15 and 16, Table II, Example 34, Table Column 7 (left to right), line 1, delete [2946] and insert --2943--.

Columns 15 and 16, Table II, Example 35, Table Column 7 (left to right), after "1240," insert -- 1140, 966, 756, (KBr)--.

Columns 15 and 16, Table II, Example 36, Table Column 8 (left to right), lines 2-3, delete [1140, 966, 756 (KBr)].

UNITED STATES PATENT AND TRADEMARK OFFICE
CERTIFICATE OF CORRECTION

PATENT NO. : 5,292,739
DATED : March 8, 1994
INVENTOR(S) : Merce-Vidal et al.

It is certified that error appears in the above-indentified patent and that said Letters Patent is hereby corrected as shown below:

Columns 17 and 18, Table III, Example 41, Table Column 12 (left to right), line 2, delete [1036] and insert --1026--.

Columns 17 and 18, Table III, Example 42, Table Column 14 (left to right), line 1, delete [2.64] and insert --2.54--.

Columns 17 and 18, Table III, Example 43, Table Column 10, delete

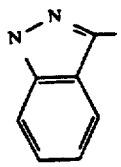

UNITED STATES PATENT AND TRADEMARK OFFICE
CERTIFICATE OF CORRECTION

PATENT NO. : 5,292,739
DATED : March 8, 1994
INVENTOR(S) : Merce-Vidal et al.

It is certified that error appears in the above-indentified patent and that said Letters Patent is hereby corrected as shown below:

and insert

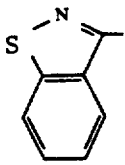

Column 19, line 40, delete [tranquillisers] and insert --tranquilizers--.

Column 24, line 56, delete [p.o.], first and second occurrence, and insert --i.p.--, first and second occurrence.

Column 25, Table VII, Title, line 1, delete [FAMILIARISATION] and insert --FAMILIARIZATION--.

UNITED STATES PATENT AND TRADEMARK OFFICE
CERTIFICATE OF CORRECTION

PATENT NO. : 5,292,739
DATED : March 8, 1994
INVENTOR(S) : Merce-Vidal et al.

It is certified that error appears in the above-indentified patent and that said Letters Patent is hereby corrected as shown below:

Column 27, line 66, delete [thiaxole] and insert --thiazole--.

Column 25, Table VII, Footnote, line 3, delete [familiarisation] and insert --familiarization--.

Signed and Sealed this

Tenth Day of January, 1995

BRUCE LEHMAN

Commissioner of Patents and Trademarks

UNITED STATES PATENT AND TRADEMARK OFFICE
CERTIFICATE OF CORRECTION

PATENT NO. : 5,292,739
DATED : Mar. 8, 1994
INVENTOR(S) : Merce-Vidal et al.

It is certified that error appears in the above-indentified patent and that said Letters Patent is hereby corrected as shown below: Title page:

Item [30]: Foreign Application Priority Data,
delete [Jan. 28, 1990 [FR] France........90 00923]
and insert —Jan. 28, 1991 [FR] France....91 00923—.

Signed and Sealed this

Twentieth Day of June, 1995

Attest:

BRUCE LEHMAN

*Attesting Officer*     *Commissioner of Patents and Trademarks*